United States Patent
Foster

[11] Patent Number: 6,047,601
[45] Date of Patent: Apr. 11, 2000

[54] SELF-TUNING CRYSTAL NOTCH FILTER

[76] Inventor: Steven G. Foster, 12101 Chapman Ave., Greenfield, Wis. 53228

[21] Appl. No.: 09/012,805

[22] Filed: Jan. 23, 1998

[51] Int. Cl.[7] ............................ G01N 29/06; G01N 29/10
[52] U.S. Cl. ............................... 73/602; 73/628; 600/447; 600/444; 600/443; 600/921
[58] Field of Search ............................ 73/602, 628, 629; 600/407, 408, 437, 442, 443, 444, 447, 449, 453, 921

[56]  References Cited

U.S. PATENT DOCUMENTS

| | | | |
|---|---|---|---|
| 3,868,605 | 2/1975 | Poole | 333/76 |
| 3,979,684 | 9/1976 | Acker | 328/167 |
| 4,232,192 | 11/1980 | Beex | 179/1 FS |
| 4,313,183 | 1/1982 | Saylors | 367/128 |
| 4,947,360 | 8/1990 | Dyer | 364/724.07 |
| 5,030,934 | 7/1991 | Kinsman | 333/188 |
| 5,148,413 | 9/1992 | Endo et al. | 367/135 |
| 5,226,057 | 7/1993 | Boren | 375/103 |
| 5,487,389 | 1/1996 | Banjanin et al. | 128/661.09 |
| 5,664,575 | 9/1997 | Banjanin et al. | 128/661.09 |

*Primary Examiner*—Hezron Williams
*Assistant Examiner*—Rose M. Miller
*Attorney, Agent, or Firm*—Dennis M. Flaherty; Christian G. Cabou; Phyllis Y. Price

[57] ABSTRACT

A self-tuning crystal notch filter suitable for rejecting a carrier signal in a receiver channel of a receiver of an ultrasound imaging system. The crystal notch filter has a resonant frequency which is electronically tuned. Tuning is done under software control without operator intervention. The software instructs a channel other than the one being tuned to transmit into the transducer. The receive channel being tuned amplifies the received signal and then passes the amplified signal through the notch filter and the TGC amplifier to the corresponding digital signal processing (DSP) circuit via an analog-to-digital converter. The software reads the amplitude of the digital receive signal output from the DSP circuit. By programming a D/A converter incorporated in the notch filter, a value can be found that minimizes the amplitude of the signal output by the DSP circuit, i.e., maximizes the amount of carrier signal being rejected. This value is then used during subsequent imaging data acquisition. This notch filter tuning operation is performed for the respective notch filter in each receive channel.

21 Claims, 2 Drawing Sheets

SELF-TUNING CRYSTAL NOTCH FILTER

FIELD OF THE INVENTION

This invention generally relates to ultrasound imaging systems. In particular, the invention relates to apparatus for beamformation of echo signals received by an ultrasonic transducer array.

BACKGROUND OF THE INVENTION

A conventional ultrasound image is composed of multiple image scan lines. A single scan line (or small localized group of scan lines) is acquired by transmitting focused ultrasound energy at a point in the region of interest, and then receiving the reflected energy over time. The focused transmit energy is referred to as a transmit beam. During the time after transmit, one or more receive beamformers coherently sum the energy received by each channel, with dynamically changing phase rotation or delays, to produce peak sensitivity along the desired scan lines at ranges proportional to the elapsed time. The resulting focused sensitivity pattern is referred to as a receive beam. A scan line's resolution is a result of the directivity of the associated transmit and receive beam pair.

The outputs of the beamformer channels are coherently summed to form a respective pixel intensity value for each sample volume in the object region or volume of interest. These pixel intensity values are log-compressed, scan-converted and then displayed as an image of the anatomy being scanned.

Referring to FIG. 1, a conventional ultrasonic imaging system comprises a transducer array 10 consisting of a plurality of separately driven transducer elements 12, each of which produces a burst of ultrasonic energy when energized by a pulsed waveform produced by a transmitter 14. The ultrasonic energy reflected back to transducer array 10 from the object under study is converted to an electrical signal by each receiving transducer element 12 and applied separately to a receiver 16 through a set of transmit/receive (T/R) switches 18. The T/R switches 18 are typically diodes which protect the receive electronics from the high voltages generated by the transmit electronics. The transmit signal causes the diodes to shut off or limit the signal to the receiver. Transmitter 14 and receiver 16 are operated under control of a master controller 20 responsive to commands by a human operator. A complete scan is performed by acquiring a series of echoes in which transmitter 14 is gated ON momentarily to energize each transducer element 12, and the subsequent echo signals produced by each transducer element 12 are applied to receiver 16. A channel may begin reception while another channel is still transmitting. The receiver 16 combines the separate echo signals from each transducer element to produce a single echo signal which is used to produce a line in an image on a display monitor 22.

Under the direction of master controller 20, the transmitter 14 drives transducer array 10 such that the ultrasonic energy is transmitted as a directed focused beam. To accomplish this, respective time delays are imparted to a multiplicity of pulsers 24 by a transmit beamformer 26. The master controller 20 determines the conditions under which the acoustic pulses will be transmitted. With this information, the transmit beamformer 26 will determine the timing and the amplitudes of each of the transmit pulses to be generated by the pulsers 24. The amplitudes of each transmit pulse will be determined by a apodization generation circuit 36 which applies respective apodization weighting factors to the pulsers. For example, the apodization generation circuit could comprise a high-voltage controller which sets the power supply voltage to each pulser. The pulsers 24 in turn send the transmit pulses to each of the elements 12 of the transducer array 10 via the T/R switches 18, which protect the time-gain control (TGC) amplifiers from the high voltages which may exist at the transducer array. The apodization weightings are generated within the apodization generation block 36, which could further comprise a set of digital-to-analog converters which take the weighting data from the transmit beamformer 26 and apply it to the pulsers 24 via the aforementioned high-voltage controllers.

The echo signals produced by each burst of ultrasonic energy reflect from objects located at successive ranges along each ultrasonic beam. The echo signals are sensed separately by each transducer element 12 and a sample of the magnitude of the echo signal at a particular point in time represents the amount of reflection occurring at a specific range.

Due to the differences in the propagation paths between a reflecting point and each transducer element 12, the echo signals will not be detected simultaneously and their amplitudes will not be equal. Receiver 16 amplifies the separate echo signals via a respective TGC amplifier 28 in each receive channel. The amount of amplification provided by each TGC amplifier is controlled through a respective control line (not shown) that is driven by a TGC circuit (not shown), the latter being set by hand operation of a respective one of a multiplicity of potentiometers. The amplified echo signals are then fed to the receive beamformer 30. Each receiver channel of the receive beamformer is connected to a respective one of the transducer elements 12 by a respective TGC amplifier 28.

Under the direction of master controller 20, the receive beamformer 30 tracks the directions of the transmitted beam, sampling the echo signals at a succession of ranges along the beam. The receive beamformer 30 imparts the proper time delay to each amplified echo signal. The receive focus time delays are computed in real-time using specialized hardware or read from a look-up table. The receive channels also have circuitry for filtering the received pulses. The time-delayed receive signals are then summed to provide an echo signal which accurately indicates the total ultrasonic energy reflected from a point located at a particular range along the ultrasonic beam. The summed receive signals are output to a signal processor or detector 32. The detector 32 converts the summed received signals to display data. Preferably detector 32 is an envelope detector. In the B-mode (grey-scale), the envelope of the signal is subjected to additional processing (commonly referred to as "post-processing"), such as edge enhancement and logarithmic compression.

The scan converter 34 receives the display data from the post-processor (not shown) and converts the data into the desired image for display. In particular, the scan converter 34 converts the acoustic image data from polar coordinate (R—θ) sector format or Cartesian coordinate linear array to appropriately scaled Cartesian coordinate display pixel data at the video rate. This scan-converted acoustic data is then output for display on display monitor 22, which images the time-varying amplitude of the envelope of the signal as a grey scale. A respective scan line is displayed for each separate transmitted beam.

Some conventional ultrasound imaging systems are capable of operation in a continuous wave mode. A continuous wave transmission has application in ultrasound imaging of the heart. When operated in a continuous wave mode, means must be provided for subtracting the carrier signal from the receive signal. Ideally about 20 dB of carrier rejection should be provided. The carrier rejection means preferably occupy very little space, use very little power and are inexpensive in order to provide a commercially viable ultrasound imaging system having a continuous wave mode.

SUMMARY OF THE INVENTION

The present invention is a self-tuning crystal notch filter suitable for rejecting a carrier signal in a receiver channel of a receiver of an ultrasound imaging system. The crystal notch filter in accordance with the preferred embodiment has a resonant frequency which is electronically tuned. Crystals cost less if a wider tolerance is permitted on the resonant frequency. By electronically tuning the resonant frequency, a lower-cost crystal can be used at the expense of the extra tuning circuitry.

In accordance with one preferred embodiment of the invention, the self-tuning crystal notch filter comprises a series dropping resistor, a simple crystal notch filter, a tuning diode, a digital-to-analog (D/A) converter and support circuitry. The tuning diode is placed in series with the crystal to tune the resonant frequency. The voltage across the diode is established by the D/A converter, a resistor arranged between the D/A converter and the tuning diode, and a resistor connected in parallel with the crystal.

In accordance with the preferred embodiment, tuning is done under software control without operator intervention. The software instructs a channel other than the one being tuned to transmit into the transducer. The receive channel being tuned amplifies the received signal and then passes the amplified signal through the notch filter and the TGC amplifier to the corresponding digital signal processing (DSP) circuit via an analog-to-digital (A/D) converter. The software reads the amplitude of the digital receive signal output from the respective DSP circuit. By programming the D/A converter, a value can be found that minimizes the amplitude of the signal output by the DSP circuit, i.e., maximizes the amount of carrier signal being rejected. This value is then used during subsequent imaging data acquisition. This notch filter tuning operation is performed for the respective notch filter in each receive channel.

DETAILED DESCRIPTION OF THE PREFERRED EMBODIMENTS

Figure 2:
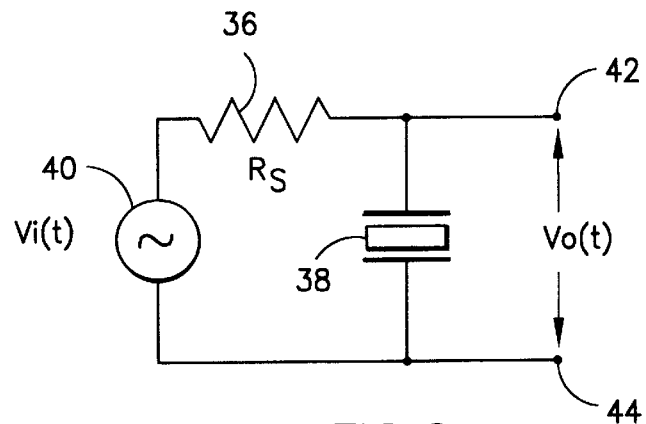
FIG. 2 is a schematic showing the circuitry of a crystal notch filter.

Crystals exhibit a series resonance where their impedance drops sharply. The series resonance frequency can be adjusted slightly by placing a capacitor in series with the crystal, as is commonly done in crystal oscillators. A simple crystal notch filter can be made from a resistor 36 having a source resistance $R_s$ and a crystal 38 connected in series across an input voltage source 40, as shown in FIG. 2. At frequencies away from the resonant frequency, the crystal's impedance can be approximated by an open circuit and the output voltage $V_o(t)$ across the output terminals 42 and 44 is almost equal to the input voltage $V_i(t)$. At the resonant frequency the crystal 38 has a low resistance and the signal is attenuated by approximately the ratio of the crystal's resistance to the source resistance $R_s$.

Figure 3:
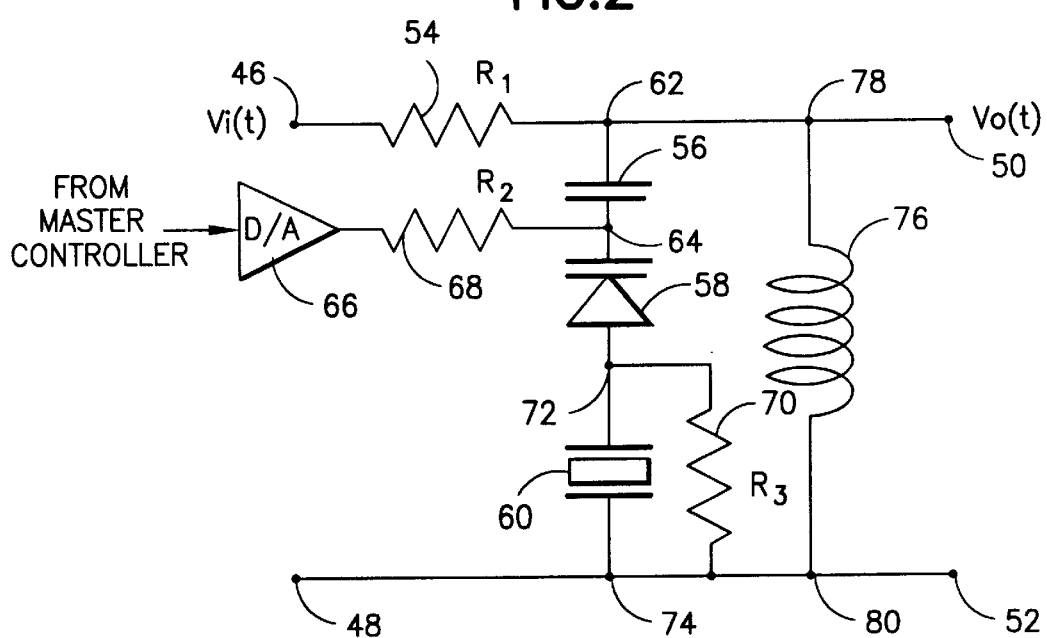
FIG. 3 is a schematic showing the circuitry of a self-tuning crystal notch filter in accordance with one preferred embodiment of the invention.

The crystal notch filter shown in FIG. 2 can be combined with additional circuitry to provide a self-tuning crystal notch filter suitable for use in rejecting the carrier signal in the receive signals in an ultrasound imaging system. Referring to FIG. 3, a self-tuning crystal notch filter circuit in accordance with a preferred embodiment of the invention is connected across voltage input terminals 46 and 48 and voltage output terminals 50 and 52. The self-tuning crystal notch filter circuit comprises a resistor 54 having a resistance $R_1$, a capacitor 56, a tuning diode 58 and a crystal 60 connected in series across the input terminals 46 and 48. A junction 62, located between resistor 54 and capacitor 56, is connected to output terminal 50. A junction 64, located between capacitor 56 and tuning diode 58, is connected to the output of a D/A converter 66 by way of a resistor 68 having a resistance $R_2$. The D/A converter 66 receives a digital input from the master controller 20 (see FIG. 1), as will be described in more detail hereinafter. A resistor 70 having a resistance $R_3$ is connected in parallel with the crystal 60 across junction 72 and 74. Junction 72 is located between the crystal 60 and tuning diode 58, while junction 74 is connected to input terminal 48 and output terminal 52. Finally, an inductor 76 is connected across junctions 78 and 80. Junction 78 is connected to junction 62 and output terminal 50; junction 80 is connected to junction 74 and output terminal 52.

Tuning diodes are specially designed to have a large change in reverse bias capacitance as the bias voltage is varied. In the preferred embodiment of the invention, tuning diode 58 is placed in series with the crystal 60 to tune the resonant frequency of the crystal. The voltage across tuning diode 58 is established by the D/A converter 66 and the resistances $R_2$ and $R_3$. In accordance with the preferred embodiment, the resistance $R_3$ is large, i.e., about 10 M $\Omega$, and serves to keep the anode of tuning diode 58 at the potential of junction 74. The anode must be kept at high impedance so that the depth of the notch will not be compromised. The resistance $R_2$ introduces the voltage of D/A converter 66 to tuning diode 58. Resistance $R_3$ should be neither so small as to load down the input voltage $V_i(t)$ nor so large as to cause a slow response to the output of D/A converter 66 by the filtering action of resistor 68 and coupling capacitor 56. Preferably the resistance $R_3$ is equal to about 100 k $\Omega$. The capacitor 56 keeps the voltage output by D/A converter 66 confined to the cathode of tuning diode 58 and preferably has a large capacitance, i.e., on the order of 0.01 $\mu$F. The inductor 76 tunes out any stray capacitance.

Figure 1:
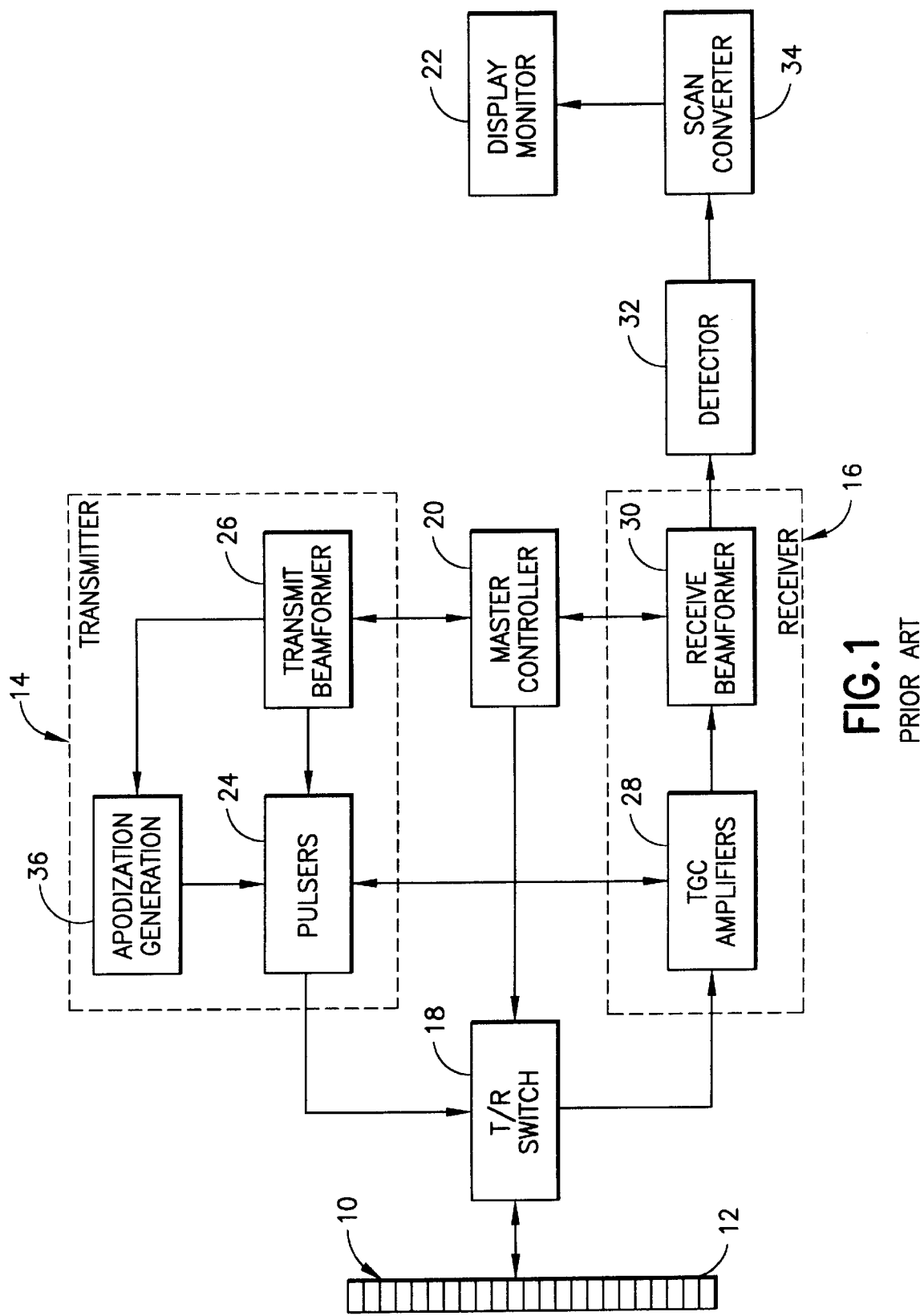
FIG. 1 is a block diagram showing a conventional ultrasound imaging system.
Figure 4:
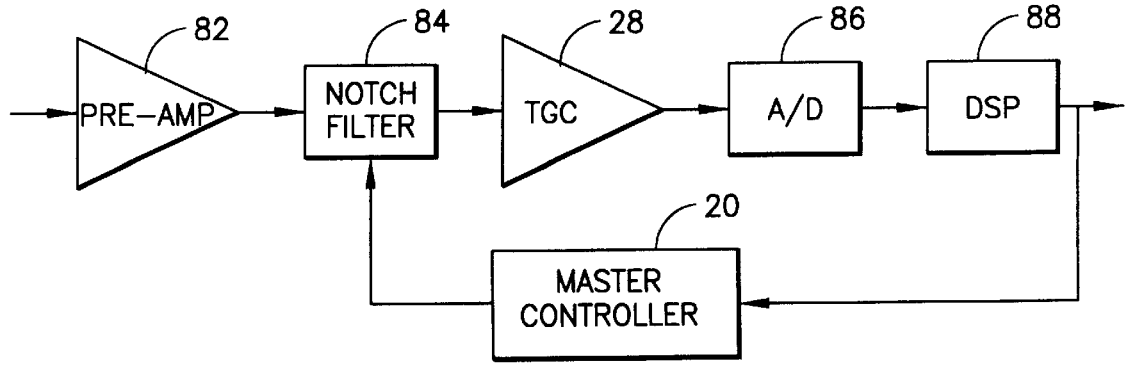
FIG. 4 is a block diagram showing one channel of a receiver in accordance with the present invention.

In accordance with the present invention, a respective self-tuning crystal notch filter circuit is incorporated in each channel of the receiver 16 (see FIG. 1). One such channel is schematically depicted in FIG. 4. The receive signal from a respective transducer array element is input to a pre-amplifier 82 via a respective T/R switch. The output of pre-amplifier 82 is connected to one of the input terminal of a self-tuning crystal notch filter circuit 84 (i.e., input terminal 46 shown in FIG. 3). The notch filter circuit is tuned to remove the carrier signal from the amplified receive signal. The filtered output signal is then input to the TGC amplifier 28. The filtered and amplified receive signal is then sampled and converted into a stream of digital values representing the amplitude of the amplified receive signal at a succession of sampling times by an analog-to-digital (A/D) converter 86.

This stream of digital samples is then input to a digital signal processing circuit 88 before undergoing scan conversion.

The notch filter circuit incorporated in the receive channel shown in FIG. 4 is tuned to the carrier frequency by the master controller 20, which stores software for performing the necessary algorithm. First, the master controller 20 outputs a first tuning value to the D/A converter 66 (see FIG. 3) of the receive channel generally depicted in FIG. 4. The master controller then instructs a channel other than the one shown in FIG. 4 to transmit into the transducer array. In response to the transmit firing of a single (or more) transducer element, the transducer element connected to the receive channel shown in FIG. 4 detects an echo signal and transduces that ultrasound echo signal into an electrical receive signal. Pre-amplifier 82 amplifies the received signal and outputs the amplified signal to the notch filter circuit 84, which is programmed in accordance with the first tuning value output by the master controller. The resulting filtered signal is then passed through the TGC amplifier 28 and the A/D converter 86 to the DSP circuit 88. The master controller 20 reads the amplitude of the digital receive signal output from the DSP circuit 88 in response to the first tuning value and stores that amplitude value. The master controller then outputs a second tuning value to the D/A converter 66 and reads the corresponding amplitude output from the DSP circuit 88. The amplitude resulting from programming of the notch filter circuit with the second tuning value is compared with the amplitude resulting from programming of the notch filter circuit with the first tuning value and the master controller stores the amplitude having the lowest value in a minimum amplitude register. This process is repeated for different tuning values until the master controller determines the tuning value which produces the minimum amplitude at the output of the DSP circuit 88.

By programming the D/A converter 66 in the foregoing manner, a tuning value can be found that minimizes the amplitude of the signal output by the DSP circuit 88. This point is at series resonance, thereby maximizing the amount of carrier signal being rejected. This tuning value is then used to tune the crystal notch filter circuit 84 during subsequent imaging data acquisition. This notch filter tuning operation is performed for the respective notch filter circuits in each receive channel of the receiver 16 (see FIG. 1).

The foregoing preferred embodiments have been disclosed for the purpose of illustration. Variations and modifications which do not depart from the broad concept of the invention will be readily apparent to persons skilled in the art. For example, it will be apparent that the amplitude of the filtered receive signal can be measured at a juncture other than the output of the DSP circuit. In particular, the amplitude can instead be measured at the output of the A/D converter 86 (see FIG. 2) or at the output of the detector 32 (see FIG. 1). All such variations and modifications are intended to be encompassed by the claims set forth hereinafter.

I claim:

1. A system for removing a signal of predetermined frequency from a receive signal in a channel, comprising:

a crystal notch filter circuit for filtering out a signal of predetermined frequency from an analog receive signal;

a tuning circuit for tuning a resonant frequency of said crystal notch filter circuit, said tuning circuit having an input for receiving a tuning value and said resonant frequency being a function of said received tuning value; and a controller having a tuning mode for outputting a succession of tuning values to said input of said tuning circuit, detecting the respective amplitudes of the filtered analog receive signal or of signals derived from said filtered analog receive signals for each of said succession of tuning values, and determining a tuning value of said succession of tuning values which produces a minimum amplitude of said respective amplitudes, and having a data acquisition mode for outputting said determined tuning value to said tuning circuit.

2. The system as defined in claim 1, further comprising an analog-to-digital converter for outputting digital samples at a sampling rate, said analog-to-digital converter being connected to receive said filtered analog receive signal or a signal derived from said filtered analog receive signal, and said controller being connected to receive a digital output of said analog-to-digital converter or a signal derived therefrom.

3. The system as defined in claim 1, wherein said crystal notch filter circuit comprises a crystal, and said tuning circuit comprises a tuning diode connected in series with said crystal.

4. The system as defined in claim 3, wherein said tuning circuit further comprises a digital-to-analog converter having an input for receiving said tuning values from said controller and having an output for sending an analog version of said tuning values to said tuning diode.

5. The system as defined in claim 4, wherein said crystal notch filter circuit further comprises first and second input terminals, a first resistance, and first and second output terminals, said second output terminal being at the same voltage level as said second input terminal, and said first output terminal being at a voltage level less than the voltage level at said first input terminal by an amount substantially equal to a voltage drop across said first resistance; and said tuning circuit further comprises a capacitance and a second resistance, wherein said first resistance, said capacitor, said tuning diode and said crystal are connected in series across said first and second input terminals, and said second resistance is connected between said output of said digital-to-analog converter and a junction located between said capacitance and said tuning diode.

6. The system as defined in claim 5, wherein said crystal notch filter circuit further comprises a third resistance connected in parallel with said crystal.

7. The system as defined in claim 2, further comprising a first amplifier connected to an output of said crystal notch filter circuit and to an input of said analog-to-digital converter, and a digital signal processor connected to an output of said analog-to-digital converter.

8. A receiver comprising a multiplicity of receive channels, a summer having a multiplicity of inputs respectively coupled to said multiplicity of receive channels, wherein each of said receive channels comprises:

a crystal notch filter circuit for filtering out a signal of predetermined frequency from an analog receive signal; and a tuning circuit for tuning a resonant frequency of said crystal notch filter circuit, said tuning circuit having an input for receiving a tuning value and said resonant frequency being a function of said received tuning value.

9. The receiver as defined in claim 8, further comprising a controller having a tuning mode for outputting a succession of tuning values to said input of said tuning circuit, detecting the respective amplitudes of the filtered analog receive signal or of signals derived from said filtered analog receive signals for each of said succession of tuning values, and determining a tuning value of said succession of tuning values which produces a minimum amplitude of said respective amplitudes, and having a data acquisition mode for outputting said determined tuning value to said tuning circuit.

10. The receiver as defined in claim 9, wherein each of said receive channels further comprises an analog-to-digital converter for outputting digital samples at a sampling rate, said analog-to-digital converter being connected to receive said filtered analog receive signal or a signal derived from said filtered analog receive signal, and said controller being connected to receive a digital output of said analog-to-digital converter or a signal derived therefrom.

11. The receiver as defined in claim 8, wherein said crystal notch filter circuit comprises a crystal, and said tuning circuit comprises a tuning diode connected in series with said crystal.

12. The receiver as defined in claim 11, wherein said tuning circuit further comprises a digital-to-analog converter having an input for receiving said tuning value and having an output for sending an analog version of said tuning value to said tuning diode.

13. The receiver as defined in claim 12, wherein said crystal notch filter circuit further comprises first and second input terminals, a first resistance, and first and second output terminals, said second output terminal being at the same voltage level as said second input terminal, and said first output terminal being at a voltage level less than the voltage level at said first input terminal by an amount substantially equal to a voltage drop across said first resistance; and said tuning circuit further comprises a capacitance and a second resistance, wherein said first resistance, said capacitor, said tuning diode and said crystal are connected in series across said first and second input terminals, and said second resistance is connected between said output of said digital-to-analog converter and a junction located between said capacitance and said tuning diode.

14. The receiver as defined in claim 13, wherein said crystal notch filter circuit further comprises a third resistance connected in parallel with said crystal.

15. The receiver as defined in claim 2, wherein each of said receive channels further comprises a first amplifier connected to an output of said crystal notch filter circuit and to an input of said analog-to-digital converter, and a digital signal processor connected to an output of said analog-to-digital converter.

16. An ultrasonic imaging system comprising a transducer array, a transmitter and a receiver each coupled to said transducer array, a signal processor coupled to said receiver, a scan converter coupled to said signal processor, and a display monitor coupled to said scan converter, wherein said transducer array comprises a multiplicity of transducer elements and said receiver comprises a multiplicity of receive channels and summing means having a multiplicity of inputs respectively coupled to said multiplicity of receive channels, wherein each of said receive channels comprises:

a crystal notch filter circuit for filtering out a signal of predetermined frequency from an analog receive signal; and a tuning circuit for tuning a resonant frequency of said crystal notch filter circuit, said tuning circuit having an input for receiving a tuning value and said resonant frequency being a function of said received tuning value.

17. The ultrasonic imaging system as defined in claim 16, further comprising a controller having a tuning mode for outputting a succession of tuning values to said input of said tuning circuit, detecting the respective amplitudes of the filtered analog receive signal or of signals derived from said filtered analog receive signals for each of said succession of tuning values, and determining a tuning value of said succession of tuning values which produces a minimum amplitude of said respective amplitudes, and having a data acquisition mode for outputting said determined tuning value to said tuning circuit.

18. The ultrasonic imaging system as defined in claim 17, wherein each of said receive channels further comprises an analog-to-digital converter for outputting digital samples at a sampling rate, said analog-to-digital converter being connected to receive said filtered analog receive signal or a signal derived from said filtered analog receive signal, and said controller being connected to receive a digital output of said analog-to-digital converter or a signal derived therefrom.

19. The ultrasonic imaging system as defined in claim 16, wherein said crystal notch filter circuit comprises a crystal, and said tuning circuit comprises a tuning diode connected in series with said crystal.

20. The ultrasonic imaging system as defined in claim 19, wherein said tuning circuit further comprises a digital-to-analog converter having an input for receiving said tuning value and having an output for sending an analog version of said tuning value to said tuning diode.

21. A method for operating an ultrasonic imaging system comprising a transducer array, a transmitter and a receiver each coupled to said transducer array, a signal processor coupled to said receiver, a scan converter coupled to said signal processor, and a display monitor coupled to said scan converter, wherein said transducer array comprises a multiplicity of transducer elements, said receiver comprises a multiplicity of receive channels and summing means having a multiplicity of inputs respectively coupled to said multiplicity of receive channels, and each of said receive channels comprises a crystal notch filter circuit, said method comprising the following steps for each receive channel:

tuning the crystal notch filter circuit to have first through N-th resonant frequencies during respective tuning cycles, where N is an integer greater than unity;

for each tuning cycle, activating said transducer array to transmit an ultrasound wave and detect a receive signal;

for each tuning cycle, inputting said receive signal to the tuned crystal notch filter circuit;

for each tuning cycle, detecting the amplitude of the filtered analog receive signal or of a signal derived from said filtered analog receive signal;

determining which one of said first through N-th resonant frequencies produces a minimum amplitude of said detected amplitudes;

tuning the crystal notch filter circuit to have said determined one of said first through N-th resonant frequencies;

activating said transducer array to transmit a transmit ultrasound beam and detect a multiplicity of receive signals after transmission of said transmit ultrasound beam; and inputting said multiplicity of receive signals to the crystal notch filter circuits of said respective receive channels after said crystal notch filter circuits have been tuned with said determined resonant frequencies.

\* \* \* \* \*